US011908565B2

(12) United States Patent
Steinberg et al.

(10) Patent No.: US 11,908,565 B2
(45) Date of Patent: Feb. 20, 2024

(54) FORCE PREDICTION FOR SPINAL IMPLANT OPTIMIZATION

(71) Applicant: MAZOR ROBOTICS LTD., Caesarea (IL)

(72) Inventors: Shlomit Steinberg, Tel Aviv (IL); Moshe Shoham, Hoshaya (IL)

(73) Assignee: MAZOR ROBOTICS LTD., Caesarea (IL)

( * ) Notice: Subject to any disclaimer, the term of this patent is extended or adjusted under 35 U.S.C. 154(b) by 255 days.

(21) Appl. No.: 17/288,660

(22) PCT Filed: Oct. 15, 2019

(86) PCT No.: PCT/IB2019/058798
§ 371 (c)(1),
(2) Date: Apr. 26, 2021

(87) PCT Pub. No.: WO2020/079598
PCT Pub. Date: Apr. 23, 2020

(65) Prior Publication Data
US 2022/0013211 A1 Jan. 13, 2022

Related U.S. Application Data

(60) Provisional application No. 62/745,489, filed on Oct. 15, 2018.

(51) Int. Cl.
*G06Q 10/00* (2023.01)
*G16H 20/40* (2018.01)
(Continued)

(52) U.S. Cl.
CPC .............. *G16H 20/40* (2018.01); *A61B 34/10* (2016.02); *G16H 30/20* (2018.01);
(Continued)

(58) Field of Classification Search
CPC ......... G16H 20/40; G16H 30/20; A61B 34/10
See application file for complete search history.

(56) References Cited

U.S. PATENT DOCUMENTS 7,458,989 B2   12/2008   Banks et al.
8,126,234 B1    2/2012   Edwards et al.
(Continued)

FOREIGN PATENT DOCUMENTS

KR   10-2018-0114438   10/2018
WO   WO 2017/221257   12/2017
(Continued)

OTHER PUBLICATIONS

International Search Report and Written Opinion prepared by the Israel Patent Office dated Jan. 20, 2020, for International Application No. PCT/IB2019/058798.
(Continued)

*Primary Examiner* — Rajesh Khattar
(74) *Attorney, Agent, or Firm* — Sheridan Ross P.C.

(57) ABSTRACT

A method for optimizing orthopedic spinal implant survival using preoperative finite element analysis combined with intraoperative stress analysis. Based on clinically relevant data, finite element analysis, and corrected values of spinal parameters, an acceptable long-term stress score is determined for an appropriate implant, which is selected from a set of potential implants, such that the shape of the implant minimizes predicted stress values. From a preoperative medical image set, values of selected spinal alignment parameters are determined; finite element analysis is performed on potential implants to determine stress values; and a selected implant is digitally positioned in the medical image set to create a virtual bone/implant configuration. After the selected implant is inserted and bent to shape, actual stress values are measured intraoperatively. The process of bending and measuring stress values is repeated until
(Continued)

the bone/implant configuration falls within the acceptable long-term stress score range.

29 Claims, 11 Drawing Sheets

(51) Int. Cl.
*A61B 34/10* (2016.01)
*G16H 30/20* (2018.01)

(52) U.S. Cl.
CPC ... *A61B 2034/102* (2016.02); *A61B 2034/105* (2016.02); *A61B 2034/108* (2016.02)

(56) References Cited

U.S. PATENT DOCUMENTS

| | | | |
|---|---|---|---|
| 8,855,389 | B1 | 10/2014 | Hoffmann et al. |
| 9,358,114 | B2 | 6/2016 | Hughes |
| 9,918,642 | B2 | 3/2018 | Hecker et al. |
| 2010/0191071 | A1 | 7/2010 | Anderson et al. |
| 2017/0231710 | A1 | 8/2017 | Scholl et al. |

FOREIGN PATENT DOCUMENTS

| | | |
|---|---|---|
| WO | WO 2018/109556 | 6/2018 |
| WO | WO 2018/131044 | 7/2018 |

OTHER PUBLICATIONS

Extended Search Report for European Patent Application No. 19873966.6, dated Jul. 15, 2022, 5 pages.

Abe et al. "Scoliosis corrective force estimation from the implanted rod deformation using 3D-FEM analysis," Scoliosis, Jan. 2015, vol. 10, Suppl 2, Article S2, 6 pages.

Galbusera et al. "Planning the surgical correction of spinal deformities: toward the identification of the biomechanical principles by means of numerical simulation," Frontiers in Bioengineering and Biotechnology, Nov. 2015, vol. 3, Article 178, 14 pages.

Xu et al. "Stress distribution in vertebral bone and pedicle screw and screw-bone load transfers among various fixation methods for lumbar spine surgical alignment: A finite element study," Medical Engineering & Physics, Jan. 2019, vol. 63, pp. 26-32.

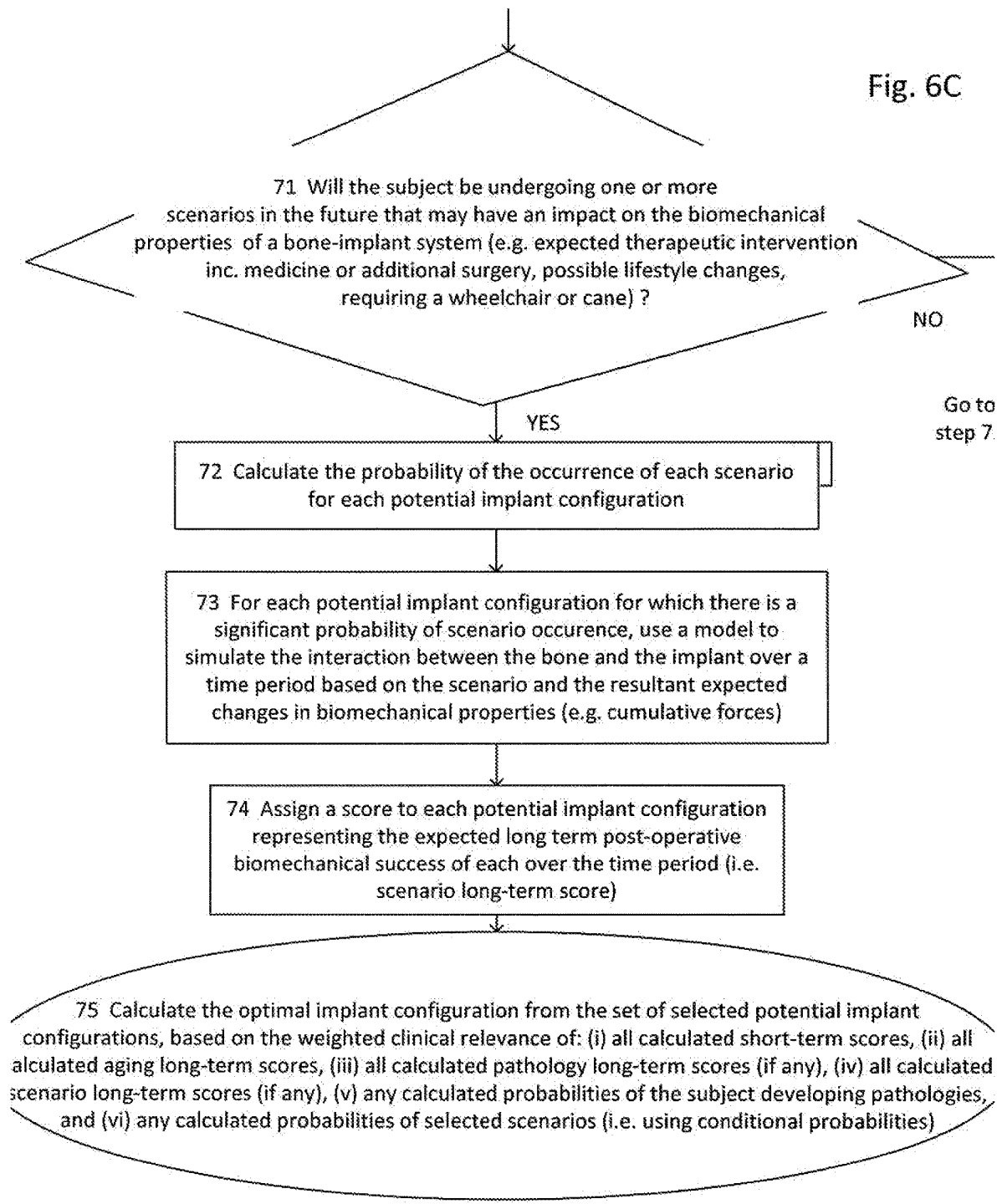

INTRA-OPERATIVE MODELING BASED ON LONG-TERM PREDICTION

76 Procedure on bone-implant system
« Perform stress analysis on bone-implant system (step 34)
« Select implant parameters based on stress analysis (step 35) and desired corrected spinal alignment parameters

77 Intraoperative modeling and long-term success prediction
«Input field pattern of strain to a model to simulate the interaction between bone and implant over time
«Determine expected changes in biomechanical characteristics of bone-implant system over time

78 Calculate the optimal implant diameter, curvature, etc.
based on anticipated long-term changes in biomechanical characteristics, taking into account corrected spinal alignment parameters

79 Modify in-situ implant
remove or adjust shape, size, composition and position of implant, or select and insert a second implant, until an implant configuration falling within acceptable stress score range is achieved

80 Implant parameters
« Accomplish optimal implant configuration to ensure long-term success of the bone-implant system in view of anticipated progressive pathology and changes in subject mobility

Figure 7

FORCE PREDICTION FOR SPINAL IMPLANT OPTIMIZATION

CROSS REFERENCE TO RELATED APPLICATIONS

This application is a national stage application under 35 U.S.C. 371 and claims the benefit of PCT Application No. PCT/IB2019/058798 having an international filing date of 15 Oct. 2019, which designated the United States, which PCT application claimed the benefit of United States Provisional Patent Application No. 62/745,489 filed 15 Oct. 2018, the entire disclosures of each of which are incorporated herein by reference.

FIELD OF THE DISCLOSURE

Embodiments of the present disclosure relate to the field of spinal instrumentation, especially for predicting and optimizing long-term implant survival and surgical outcomes.

BACKGROUND

Low back pain resulting from instability of the axial skeleton causes debilitation and necessitates large numbers of operations annually for lumbar spine stabilization. Other causes of spine-related debility requiring surgical stabilization include kyphosis, scoliosis, and other abnormal curvatures of the spine. Some surgical procedures to immobilize adjacent vertebrae use intervertebral rods to stabilize and straighten the spinal column. Because of the strong forces generated on both the spinal column and the implanted rods, many such spinal instrumentation operations fail to accomplish fusion of the instrumented bones, or the implants even fail, leading to pain, disability, and the need for revision treatment. Such failures necessitate additional surgical procedures, almost always more complicated and difficult than the first, to attempt to relieve the disability and to correct the lack of success.

Moreover, a number of secondary spine-related pathologies may develop over time, due to the stress on the bone-implant system. Some of these secondary pathologies include adjacent level degeneration at a vertebra or intervertebral disc adjacent to a surgical fusion; adjacent segment disease adjacent to a surgical fusion necessitating revision surgery; proximal junctional kyphosis; proximal junctional failure; and kyphotic decompensation syndrome, a progressive sagittal deformity requiring revision surgery for spinal realignment. These pathologies may develop many months, years or even decades after a surgery, often requiring revision surgery. Furthermore, after a period of time following the surgery, post-operative instrumentation failures may occur, such as screw pull-out and implant breakage. These delayed failures can result from the secondary pathologies, or from such factors as progressive scoliosis in neuromuscular disease, progressive osteoporosis in aging or chronic steroid treatment, overuse injury, and excessive weight gain.

Today it is understood that the development of pathologies and instrumentation failures in patients, following spinal operations, is strongly related to preoperative and post-operative spinal alignment parameters, as may be determined from three-dimensional images, as well as to the degree of anatomical adjustment during the surgery, and that a planned spinal surgical technique should take these factors into consideration, as clinically relevant patient specific risk factors.

Prior efforts have attempted to calculate the intraoperative forces to optimize a bone implant for joint replacements; however, these previous endeavors were for application to bones and joints other than the spine, which is a much more complex orthopedic and neurological system. Some such references include U.S. Pat. No. 9,358,114 to M. D. Hughes for "Intraoperative Scanning for Implant Optimization", a method for implanting an implant relative to a joint, relevant for knee arthroplasty; U.S. Pat. No. 7,458,989 to Banks et al. for "Intraoperative Joint Force Measuring Device, System and Method", measuring joint loads during surgery, relevant for joint replacement surgeries; and U.S. Pat. No. 8,855,389 to Hoffmann et al. and U.S. Pat. No. 8,126,234 to Edwards et al., both for "Automated Patient-Specific Bone-Implant Biomechanical Analysis". In these latter two patents, the planning is based on a 'digital library of generic bone-implant finite element meshes' and not according to the actual bone-implant relation. The methods in the aforementioned references measure intraoperative forces; they do not predict long-term outcomes.

U.S. Pat. No. 9,918,642 to Hecker et al., describes a biological pressure measuring device that comprises fiber Bragg grating sensors (FBG sensors), but not for intraoperative measurements. Sato et al. in an article entitled "A comparative evaluation of the hybrid technique for fixation of the sagittal split ramus osteotomy in mandibular advancement by mechanical, photoelastic, and finite element analysis" published in Oral Surg. Oral Med. Oral Pathol. Oral Radiol. 2012; Vol. 114 (suppl 5); pp. S60-S68, describes various methods of stress measurements on synthetic models of instrumented bones.

Attempts have been made to predict the long-term effects of various types of spinal interventions on the discs adjacent to the fused vertebrae by using finite element analysis; as for example, in the article by Srinivas et al., entitled "Long-Term Effects of Segmental Lumbar Spinal Fusion on Adjacent Healthy Discs: A Finite Element Study", published in Asian Spine J 2016; 10(2):205-214. Such virtual analysis allows prediction of the probable long-term effects of a given surgical intervention, but does not provide actual data related to a particular implant in real time. The above mentioned U.S. Pat. No. 8,855,389 for "Automated patient-specific bone-implant biomechanical analysis" to Hoffman et al. describes a method for biomechanical analysis of a bone-implant system having only a bone-implant analysis without providing real-time analysis of load on the bone-implant system. Commonly owned International patent publication number WO/2018/131044, filed in the US as application Ser. No. 16/509,630, and herewith incorporated by reference in its entirety, describes a method using image-based pathology and artificial intelligence for predicting outcomes in spinal surgeries.

The disclosures of each of the publications mentioned in this section and in other sections of the specification, are hereby incorporated by reference, each in its entirety.

SUMMARY

There exists a need for a method which overcomes at least some of the disadvantages of prior art systems and methods, to not only determine intraoperative forces, but also to predict the level of force on an implant which will give rise to favorable long-term surgical outcomes and long term bone-implant survival.

A challenge in the field of surgical correction of spinal deformities is the need to both provide a straighter spinal column and an implant system that will survive long-term.

As the stress placed on a straightened spine by the implants may lead to pull-out of the screws or predispose to failure of the implant itself, the stress measurements and the optimal spinal correction may trend in opposite directions. Thus, there is a need to provide a compromise between the need for optimal correction of a spinal deformity, which may require use of a highly stressed rod, and the need for a long lifetime prediction, which may be more limited because of the high level of forces applied to the rod.

The present disclosure describes new exemplary systems and methods for optimizing spinal implant survival using preoperative finite element analysis of the implant combined with intraoperative photoelastic stress analysis. In the first phase of the method, preoperative image-based prediction, as discussed in the above mentioned WO/2018/131044, is combined with finite element analysis of the bone-implant system and its preselected implants, virtually positioned in situ within the vertebrae they are meant to fuse or realign. In this disclosure, different implants are understood to be differentiated as being either implants having different physical properties, such as in length, thickness, or material, or a single, physical implant differently shaped by adjusting its curvature, or a multiple component implant configuration. The finite element analysis produces a determination of stress scores on elements along the length of the bone-implant system. These stress scores indicate the level of post-operative stress likely to be placed on each individual rod component of the entire implant system at each point along its extent. The regions of contact between pedicle screws and bones, between pedicle screws and rods, and within specific parts of each implant component, comprise the regions of greatest potential stress to be considered by the system.

The predicted stress scores are calculated for a series of time points, both short-term and over time. The acceptable short and long-term stress scores will differ for a given subject depending at least on his/her specific combination of relevant demographic features, BMI, bone density, instrumentation needs, current or future predicted pathologies, anticipated level of activity, and expected lifespan. Preoperative patient data input to a prediction software allows additional calculations regarding likelihood of development of given bone pathologies and other long-term outcomes. A set of acceptable stress scores is determined for each selected implant component that will enable the greatest chances of long-term, overall bone-implant survival. The prediction is based on results of previous spinal correction procedures on other patients, which are tracked by a large database containing relevant long-term information on patients having undergone the same type of procedure, whether spinal fusion or deformity correction. For a given patient, the preoperative analysis including finite element analysis and statistical predictions of future patient health status scenarios, will be incorporated into the prediction algorithm. The rod or rods to be implanted are selected and contoured according to the experience of the surgeon or other medical practitioner performing the procedure, or in coordination with a machine generated plan, to provide an adequate solution to the patient's pathology, and to have resulting stress scores along the entire length of the bone-implant system, that fall within the predetermined acceptable range. A stress score within the indicated acceptable range for that patient signals that the proposed rod shape and dimensions are acceptable in providing a long term solution to the patient's problem. A stress score outside of the indicated acceptable range for that patient, signals that the proposed rod shape and dimensions are unacceptable and an alternative bone-implant configuration needs to be selected.

The procedure, in more detail, includes the following steps:

Preoperative data is collected and input to a prediction software. The collected data include at least some of:
 (i) patient demographic data including but not limited to age, gender, ethnicity, height, weight and BMI;
 (ii) preoperative clinical data including bone density measurement, comorbidities using the Charlson Comorbidity Index (CCI), American Society of Anesthesiologists grade (ASA) and diagnosis; health qualifying factors such as whether the patient is a smoker and how many cigarettes per day;
 (iii) spinal alignment parameters such as, but not limited to, thoracic kyphosis, lumbar lordosis, cobb, spinal vertical axis, pelvic incidence-lumbar lordosis mismatch, pelvic tilt, sacral slope;
 (iv) spinal stability parameters such as spondylolisthesis grade, inter-facet distance, stenosis, disc height ratio and range of motion; and
 (v) radiographic data including 2D x-ray scans and 3D CT and/or MRI scan, and/or other medical images.

The surgeon either selects a set of potential implants based on his/her prior experience, or instructs the system to select a set of potential implants, based on machine learning and information gathered from at least one medical database. The system uses statistical analysis, big data and artificial intelligence analysis in combination with patient data to assist in selection of a set of potential implants, including a maximal allowable stress score for each individual implant in a given patient. A computerized assessment using finite element analysis, which indicates the stress distribution along the implant and the ensuing strains, is then carried out to determine the likely success of each bone-implant system under various levels of mechanical stress. Additional relevant biomechanical measurements include the overall displacement of the implant under a given applied force to the implant, which provides a quantitative measure of implant stability. Further implementations of this scenario could be added with acquisition of more data, better imaging and improved techniques for determining clinically relevant parameters.

Based on the finite element analysis and assessment of implant stability, optimal implant characteristics are selected, including at least some of length and diameter, material and composition, curvature or shape, position and orientation in relationship to the vertebra height, depth and angle. Other factors to consider in the selection of the optimal implant include the identity and number of vertebrae to be fused, and the location of upper and lower instrumented vertebra. Subsequently, for each patient and for each implant configuration, an acceptable level of stress on the bone-implant system is selected according to the finite element analysis and preoperative patient data subjected to big data, statistical analysis and artificial intelligence assessment.

The second phase of the method is an intraoperative stage, carried out physically during the surgical procedure itself, in which preselected implants, coated with a photo-elastic material, are bent to a shape consistent with the desired correction for the patient, and are subjected to photo-elastic stress analysis. The initial planned shape is determined by the preoperative plan as determined by the above described prediction procedure, and may be modified by the surgeon intraoperatively. The photoelastic analysis is performed on the selected bone-implant system, revealing in the display system, the actual strain distribution along the length of the implant. The surgeon can adjust the contours of the implant to reduce the stress on the bone-implant system, such that the stress scores fall within the predetermined acceptable range. In the preoperative modeling, additional outcomes to consider include strength of the bone-implant construct under very high or hypothetical loading conditions, e.g., the failure of a rod at a certain position along its length, or the axial pull-out limit of a pedicle screw. Output could include risk estimates of local failure of the bone-implant system. The intraoperative stress analysis thus provides a series of stress scores on the different potentially acceptable shapes of an implant parallel to the preoperative virtual finite element analysis. This series is then compared to the predetermined acceptable stress score range assigned preoperatively.

A novelty of this step of the method is that it allows the surgeon to optimize the surgical outcome based on intraoperative stress analysis, rather than relying solely on preoperative surgical planning.

Unlike the methods of the prior art which consider only the future configuration of the subject's bone, some of the presently disclosed methods consider the interrelationship of the bone and implant, for use in predicting long-term survival of the bone-implant system and optimizing surgical outcomes by reducing the risk for implant failure such as, but not limited to, proximal junctional kyphosis, proximal junctional failure, distal junctional kyphosis, distal junctional failure, adjacent level disease.

Furthermore, unlike the methods of the prior art which determine an optimal surgical plan based only on the current bone configuration and mechanical properties, the presently disclosed methods may be used to determine the optimal implant configuration, based on predicted changes over time of the bone-implant system. Such predicted changes over time take into consideration the effects of subject aging, smoking, cancer or other pathology, and resulting bone density changes; implant fatigue failure; bone and implant stress from correction of the original spinal misalignment; number, size, and placement of rods and screws; rod composition, bending, and implant construction; and other factors related to the impact of the instrumentation on the patient's physiology. For example, in adult deformity surgery, the presence of postoperative positive sagittal imbalance and residual increased thoracolumbar kyphosis have higher incidences of failure. These are two areas of stress concentration and transition. Failure of fusion and loosening of instrumentation in the thoracolumbar and the lumbosacral spine areas may be related to the increased tensile and shear forces on the bone-implant system.

Using the database and applying machine learning or other form of artificial intelligence, the prediction may be performed for multiple future time points, including time points years or decades away. In an advantageous implementation, dynamic models or virtual simulations of the mutual interaction of the bone-implant system may also be used. In determining the predicted mutual interaction over time of the bone-implant system, it is preferable to perform an analysis of the entire spine of the subject. Spinal parameters of relevance have been defined above. For example, excessive lumbar lordosis may increase the forces acting on the vertebra(e) of interest, having an effect not only on current biomechanical properties of a rod inserted to support the vertebrae of interest, but also having an effect on future forces as the lumbar lordosis increases over time in certain pathological states. In patients with muscular weakness from dystrophy or other progressive causes, kyphosis and scoliosis may tend to worsen over time, placing additional stress on the bone-implant system. In determining the mutual evolution of the bone-implant system, osseo-integration of the implant over time is also considered, since creation of a strong implant-bone interface is an important factor in structural, bio-mechanical and functional stability.

All of these factors may be taken into account by the system as it applies machine learning to the database and considers particular features of a given patient. Modeling the bone-implant system over the long-term is accomplished using big data analysis and predictive models. Furthermore, in operated patients whose bone-implants fail and who return for revision operation, the survival of the implant according to stress score can be calculated by modeling, thus providing retroactive information that can further be used for planning the spinal correction in future patients. The relative parameters to be incorporated in the model include at least preoperative surgical planning, intraoperative stress scores, post-operative imaging, and calculation of stress using finite element analysis. Thereby, correlations between the stress scores and patient outcomes can be determined, and thus also the threshold or optimal stress score for long-term bone-implant survival.

According to other implementations, the implants or accompanying instrumentation such as screws, may be equipped with sensors that measure the load postoperatively in real time and transmit the output to an application monitored by the user, who is updated in real time regarding the load level. Based on this output, the user may perform correction to his/her activity or position if needed. This option is a backup for the preoperative and intraoperative analysis, which is designed to prevent the need for such correction. Long-term follow up may also be accomplished by radiographic imaging, subject feedback by repeated assessments using Oswestry Disability Index (ODI) and clinical evaluation.

A related method of modeling and predicting long-term success of a bone-implant system adds the following step during the intraoperative implantation procedure: insert into a subject's spine a selected implant, the implant being adapted to have at least one mode of stress detection. Measure the stress at each point along the element with the relevant mode of stress detection, in order to obtain a field pattern of stress of the implant. Still intraoperatively, input the field pattern of stress to a model to simulate the interaction between the bone and the implant over a given time period to determine expected changes in the field pattern of stress over that time. Finally, based on these expected changes in the field pattern of stress, calculate the optimal shape of the implant to fall within the predetermined acceptable stress score over a given time period. Based on the long-term prediction calculations above, bend the implant until an implant configuration falling within the acceptable long-term stress score is achieved.

A third related method for long-term follow-up of bone-implant success, comprises using an implant equipped with at least one mode of stress detection able to provide remote, real time measurement of stress on the bone-implant system. At regular intervals of time post-operatively, determination of spinal parameters (sagittal/coronal Cobb, TK, LL, SVA, SS, PI, PT, AVT-T, AVT-L, CD, RAD, and pelvic obliquity) is accomplished by analysis of medical images and field pattern of stress by finite element analysis. Real-time feedback of spinal parameters and field pattern of stress is provided to the surgeon. Data are stored and evolution of spinal parameters and the field pattern of stress of bone-implant system are followed over time. Review of the data following evolution of the bone-implant system allows the surgeon to provide long-term feedback. This method may use least one of big data analysis, statistical analysis, and modeling of feedback of stress scores for the individual subject according to long-term stress score.

A further variation of this method for long-term follow up and prediction of spinal instrumentation is one in which modeling is based on a database of information, such as a tangible, non-transitory, computer-readable storage medium, collected from subjects undergoing operations for bone-implant systems, or uses pre-operative planning with finite element analysis to analyze survival of the bone-implant system of subjects who return for revision operation of a bone-implant system.

There is further provided, in accordance with other exemplary implementation of the methods and systems of the present disclosure, a method of determining an optimal, long-term orthopedic implant configuration for a spinal alignment correction procedure in a subject, comprising:
  (a) based on a set of preoperative medical images, determining initial values and a desired corrected set of values of selected spinal alignment parameters,
  (b) selecting at least one potential implant for correcting the selected spinal alignment parameters,
  (c) digitally positioning, in the set of preoperative medical images, the at least one potential implant for correcting the selected spinal alignment parameters, to create at least one virtual configuration of at least one potential bone-implant combination,
  (d) determining an acceptable long-term stress score range for the at least one virtual configuration based on (i) clinically relevant data of the subject, and (ii) similarly characterized cases from a medical database,
  (e) for the at least one virtual configuration, (i) performing finite element analysis on the at least one potential implant to determine stress scores along an extent of the at least one potential implant, and (ii) calculating expected corrected values of the selected spinal alignment parameters,
  (f) select an implant from the at least one potential implant, which minimizes the long-term stress score,
  (g) intraoperatively, inserting the selected implant into the spine of the subject, the inserted implant being adapted to have at least one mode of stress detection,
  (h) using the at least one mode of stress detection, intraoperatively measuring a stress score at each point along the length of the inserted implant, and
  (i) modifying the inserted implant and repeating steps (g) to (h) until an implant configuration falling within the acceptable long-term stress score range is achieved.

In such a method, if no implant configuration falling within the acceptable long-term stress score range is achieved, steps (f) to (i) are repeated with a second implant from the at least one potential implant, until an implant configuration falling within the acceptable long-term stress score range is achieved. In either of the above described methods, the implant configuration falling within the acceptable long-term stress score range should have a combination of corrected spinal alignment parameters, minimum stress score, and maximum long term survival, to thus provide an optimal long-term orthopedic implant configuration. Furthermore, modifying the inserted implant may comprise modifying at least one of the shape, curvature, or orientation of the inserted implant.

In additional implementations of the above described methods, the inserted implant may comprise a photoelastic coating, and the step of intraoperatively measuring a stress score may use photoelastic analysis of the photoelastic coating to obtain a field pattern of stress of the implant in situ.

Additionally, in any of the previous methods, force measurement may be accomplished by sensors of the fiber Bragg grating type, or may be accomplished by tactile force feedback from the surgical robot. Furthermore, stress analysis may be carried out using sensors connected to a screw saddle or to a fusion rod. Furthermore, the implant may comprise any of pedicle screws, interbodies and rods, and at least one of the shape, size, composition, orientation and position of a preselected implant may be replaced by a different implant. Additionally, potential implant configurations may comprise at least one of the shape, size, length, diameter, composition, position and orientation of each implant.

According to further implementations of the above described methods, the pre-operative medical images are at least one two-dimensional or three-dimensional CT, MRI, X-ray, and dynamic motion capture images. Additionally, spinal alignment parameters may comprise at least some of Sagittal/Coronal Cobb, TK, LL, SVA, SS, PI, PT, AVT-T, AVT-L, CD, RAD, Pelvic obliquity.

In any of the methods, the long-term acceptable stress score may be calculated per patient. Additionally, the implant may comprise at least one intervertebral rod and at least two pedicle screws and the properties of the implant may comprise at least one of a shape, diameter, length, and material composition.

In these methods the selected bone/implant combination may be chosen to correct the spinal alignment parameters better than other potential bone/implant combinations. Additionally, the clinically relevant information may comprise at least one of (i) past medical history, (ii) age, (iii) BMI, (iv) gender, (v) comorbidity, (vi) ethnicity, and (vii) current clinical status.

Finally, these methods may use pre-operative planning using the finite element analysis to analyze survival of the bone-implant system of subjects who return for revision operation of the bone-implant system.

According to a further implementation described in this disclosure, there is provided a surgical system for determining an optimal long-term orthopedic implant configuration for a spinal alignment correction in a subject, comprising:
  a control unit comprising (i) a module for finite element analysis of orthopedic configurations, (ii) an analytic engine for evaluating the long term effect of implant configurations using previous cases documented in a large database, (iii) a calculating unit for determining spinal alignment parameters from a virtual configuration of a spine corrected using a spinal implant arrangement, (iv) a comparator unit for determining whether a predicted stress score of an implant configuration falls within a predetermined acceptable stress score for long term sustainability, the control unit being configured to determine an optimal implant configuration, by:
    (a) based on a set of preoperative medical images, determining initial values and a desired corrected set of values of selected spinal alignment parameters,
    (b) selecting at least one potential implant for correcting the selected spinal alignment parameters,
    (c) digitally positioning, in the set of preoperative medical images, the at least one potential implant for correcting the selected spinal alignment parameters, to create at least one virtual configuration of at least one potential bone-implant combination, (d) determining an acceptable long-term stress score range for the at least one virtual configuration based on (i) clinically relevant data of the subject, and (ii) similarly characterized cases from a medical database, (e) for the at least one virtual configuration, (i) performing finite element analysis on the at least one potential implant to determine stress scores along an extent of the at least one potential implant, and (ii) calculating expected corrected values of the selected spinal alignment parameters, and (f) selecting an implant from the at least one potential implant, which minimizes the long-term stress score, and a system for measuring the stress in an implant inserted onto the spine of a subject, the system comprising a camera adapted to determine the stress patterns arising in the implant by analyzing an image of the photoelastic coating on the inserted implant, the system being thus configured to enable the adjustment intraoperatively of the at least one potential implant to minimize its stress score, thereby providing an improved long term orthopedic implant configuration.

24. A method of modeling and predicting long-term success of a spinal implant configuration in a subject, comprising:

(a) for a plurality of potential implants, calculating a long term stress score for at least one potential implant based on (i) stress within the at least one potential implant as determined using finite element analysis of a virtual configuration of the at least one potential implant virtually inserted into a preoperative image of a spine of a subject, (ii) calculated values of selected spinal parameters, and (iii) clinical data of the subject and from a database of similar cases, (b) determining an acceptable long-term stress score range for the virtual configuration of the at least one potential implant based on (i) clinically relevant data of the subject, and (ii) similarly characterized cases from a medical database, (c) if the long term stress score for the for at least one potential implant does not fall within the acceptable long-term stress score range, selecting another potential implant from the plurality of potential implants, until the stress score of an optimal one of the potential implants falls within the acceptable long-term stress score range, (d) intraoperatively inserting the optimal implant into the subject, the implant being adapted to have at least one mode of stress detection, (e) using the at least one mode of stress detection to measure a stress at points along the inserted optimal implant to obtain a field pattern of stress of the inserted implant, (f) inputting the field pattern of stress to a model to simulate an interaction between the spine and the inserted optimal implant over a given time period to determine expected changes in the field pattern of stress over the given time period, (g) based on the expected changes in the field pattern of stress, calculating an optimal shape of the inserted optimal implant that causes the inserted optimal implant to have a minimum long term stress score over the given time period, and (h) based on the calculations of step (g), adjusting the inserted optimal implant to the calculated optimal shape.

According to a further implementation described in this disclosure, there is provided a method for long-term follow-up of bone-implant success in a subject, comprising:

(a) selecting an optimal implant from a plurality of potential implants based on (i) stress within the plurality of potential implants detected using finite element analysis of a virtual configuration of each of the plurality of potential implants virtually inserted into a preoperative image of a spine of a subject, (ii) calculated values of selected spinal parameters, and (iii) clinical data of the subject and from a database of similar cases, (b) determining an acceptable long-term stress score of the optimal implant for the subject, (c) intraoperatively inserting the optimal implant into the subject to yield a bone-implant system, the optimal implant being equipped with at least one mode of stress detection able to provide remote, real time measurement of stress on the bone-implant system, (d) determining, at regular intervals of time post-operatively, selected spinal parameters by analysis of medical images and by finite element analysis of a field pattern of stress detected with the at least one mode of stress detection, (e) providing real-time feedback of the selected spinal parameters and of the field pattern of stress to at least one of the subject and a surgeon, and (f) measuring evolution of at least one of the spinal parameters and of the field pattern of stress of bone-implant system In such a method the selected spinal parameters may comprise at least one of sagittal/coronal Cobb, TK, LL, SVA, SS, PI, PT, AVT-T, AVT-L, CD, RAD, and pelvic obliquity. Additionally, the method may further use at least one of big data analysis, statistical analysis, and modeling of the feedback of stress scores for the individual subject according to the long-term stress score. In such a case, the modeling may be based on a database of information collected from subjects having undergone spinal implant operations.

BRIEF DESCRIPTION OF THE DRAWINGS

The present invention will be understood and appreciated more fully from the following detailed description, taken in conjunction with the drawings in which:

FIGS. 6A to 6C detail each step of the preoperative virtual bone-implant analysis of FIGS. 2 and 3, illustrating how the optimal implant is selected;

FIG. 7 illustrates the steps of performing the intra-operative modeling of FIG. 3 but based on long-term predictions of anticipated progressions in the pathology or clinical status of the patient;

DETAILED DESCRIPTION

Figure 1:
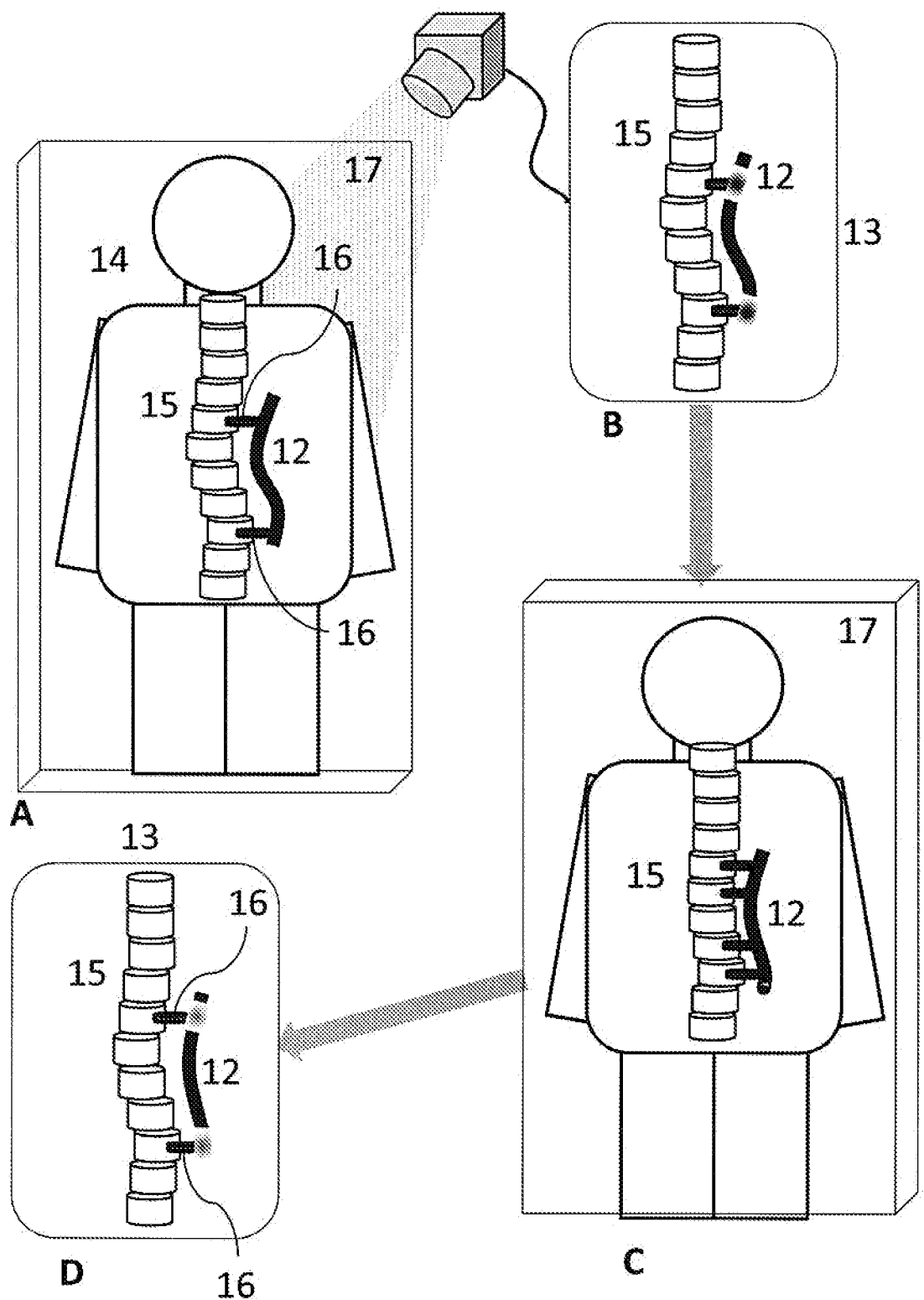
FIG. 1 illustrates schematically, an exemplary system, use of which enables the performance of a method of the present disclosure.

Reference is now made to FIG. 1, which illustrates schematically, an exemplary system, use of which enables the performance of a method of the present disclosure, for the practical adoption of potentially acceptable bone-implant systems to optimize bone-implant integration and functionality over time. In step A, the subject 14 is shown lying on the operating table 17 during a surgical implant procedure of the subject's spinal column 15. The implant 12, which in this case is a multi-level spinal fusion rod, is chosen having a shape according to a preoperative plan, or a surgeon's adaption thereof, and having been subjected to an analysis for adaption to the patient's clinical situation. The implant rod or rods has a photoelastic coating on the outer surface, or another type of stress sensor connected thereto, and is attached by pedicle screws 16 or other hardware, to the vertebral positions to be fused or to the vertebral region to be repositioned. A real-time imaging device 11 such as, but not limited to, a CCD camera or scanner, images the relevant region of the spine, including the implant 12. The camera system, or the system controller and its associated computing system, displays and may record the photoelastic stress analysis, and the output is used to generate the stress distribution on the implant, which may be displayed on a monitor 13, in real time. The stress distribution s shown schematically by the lighter shaded parts near the attachments of the rod to the pedicle screws shown. A calculation may then be performed, by comparing predetermined acceptable stress levels for long-term duration, as will be explained below, with the current stress distribution at different points along the implant, to provide feedback to the surgeon to indicate which, if any, areas of the contoured rod implant fall outside the allowable stress score. Although the implant used in this exemplary implementation is a single multi-level rod, it is to be understood that the method may also be performed on a series of single intervertebral rods, making up a complete multi-rod implant configuration.

If the first stress score analysis illustrated in step B is not deemed acceptable, the surgeon may remove the rod, reshape it, optionally amend its attachment positions, and reinsert it, and the photoelastic analysis is then repeated, as shown in step C. This procedure can be repeated more often, in order to determine an acceptable stress level for the contour of the implant used. The surgeon adjusts the shape of the implant until acceptable stress levels are achieved, at which point the surgical fusion procedure is completed, as shown in step D, where an acceptable stress score is achieved. Details of this process are further described in the following figures. A novelty of this method is that it allows the surgeon to optimize the surgical outcome based on intraoperative stress analysis, rather than relying solely on preoperative surgical planning.

Figure 2:
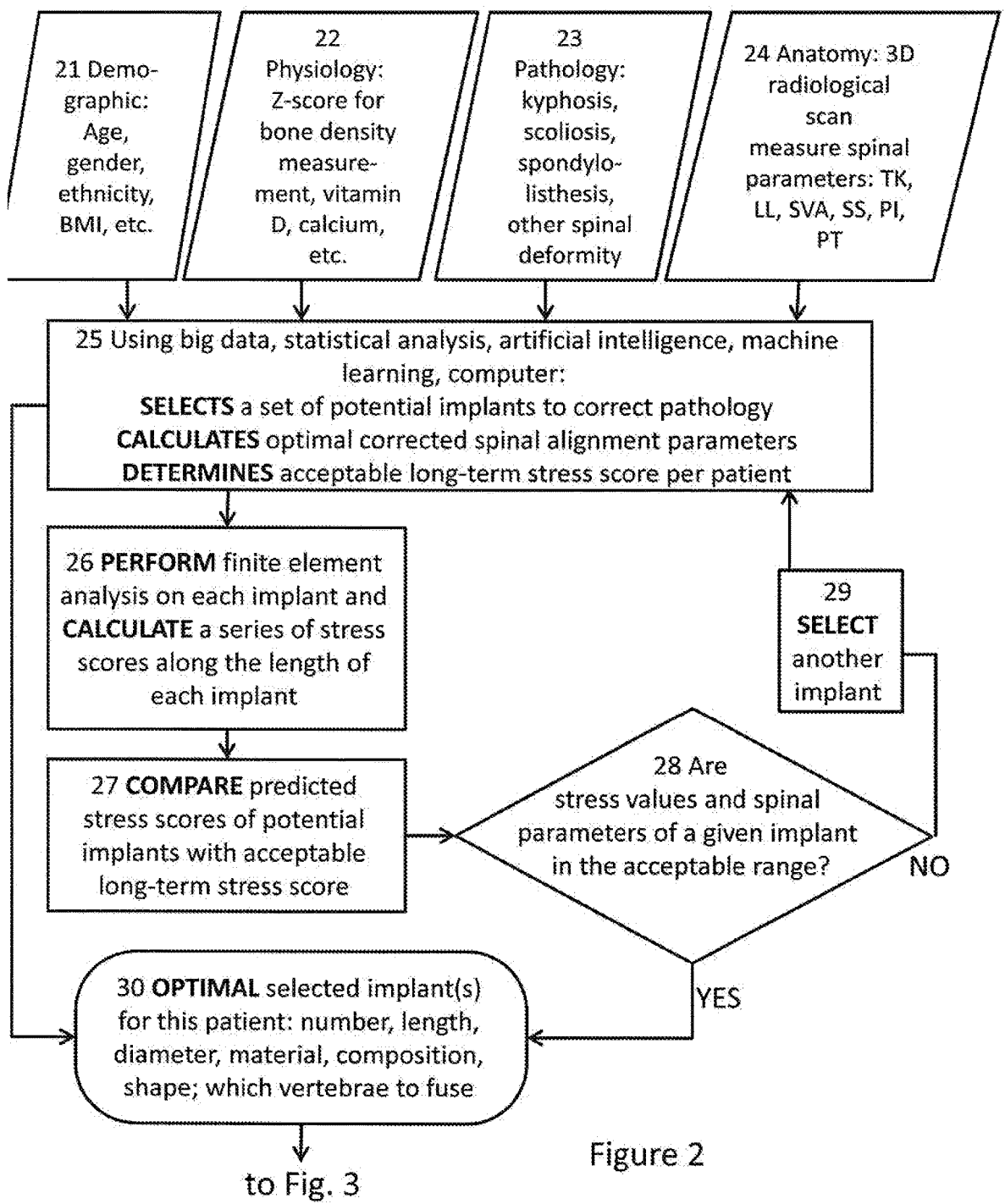
FIG. 2 is a flow chart of an exemplary method of calculating preoperatively, the predicted long-term stress score of a spinal implant.

Reference is now made to FIG. 2, which illustrates a flow chart of an exemplary method of calculating preoperatively, the predicted long-term stress score of a spinal implant. In steps 21-24, various categories of patient data are input to the system. Such detailed data may include demographics (21), physiological/clinical parameters (22), pathological diagnosis (23), and radiographic studies (24). Demographic data 21 may include at least some of subject age, gender, ethnicity, weight, height, and body mass index. Clinical parameters 22 may include at least some of bone density Z-score, serum vitamin D and calcium levels, and comorbid conditions. Pathological input 23 may include at least the clinical diagnosis and type of spinal deformity present. Anatomical data 24 is acquired in the form of 2D or 3D radiographic images of the spinal column of at least the area to be surgically corrected. Spinal alignment parameters that define the spinal pathology or deformity are then calculated from the radiographic images 24. Such parameters may include at least some of sagittal/coronal Cobb angles, thoracic kyphosis (TK), lumbar lordosis (LL), sagittal vertical axis (SVA), pelvic incline (PI), sacral slope (SS) and pelvic tilt (PT), apical vertebral translation-thoracic (AVT-T), apical vertebral translation-lumbar (AVT-L), CD, RAD, and pelvic obliquity.

In step 25, based on computerized analysis of the data input in steps 21-24, and also including data obtained from one or more large databases of spinal deformities and their long-term success or lack of success in correction of the spinal deformities involved in each case, and using statistical analysis and artificial intelligence, a determination of an optimal spinal alignment and suitable implant(s) needed to accomplish that optimal alignment, is derived, from which determination of a set of potential implants can be obtained, including at least one of the shape, size, length, diameter, composition, position and orientation of implant. Based on the predicted interaction between the implant and the spine, corrected spinal alignment parameters are calculated, and acceptable stress scores for each implant are determined. The implant or implants are virtually positioned on the radiological or other images of the spinal column in correct juxtaposition to the vertebrae to be instrumented. Repeated calculation, as was done in step 24, is performed of the spinal parameters for each bone-implant combination. In step 26, each potential bone-implant combination is then subjected to finite element analysis, as is known in the biomechanical arts. The stress values along the length of each implant are calculated, and an overall stress score is determined for the complete bone-implant system, based on biomechanical analysis of stress values along the length of the individual implants.

In step 27, this overall stress score is compared with the long-term stress score defined in step 25 as being acceptable for that patient. These long-term stress scores are determined based on input from a database of patients and their clinical course over time, such that the accuracy of the predication will increase with more patients and longer follow up. The stress values and spinal parameters resulting from the selected implant are compared in step 28 with the values considered to be within the acceptable range, and if not, another implant configuration is selected in step 29 for repeating the process of steps 25 to 28. The characteristics of the unsuccessfully selected implant may optionally be added to the database as such, in order to increase the information on useful and less useful implants for future selection criteria. If on the other hand, the stress values and resulting spinal parameters are within the acceptable range, then that implant is determined to be an optimal implant for this patient, as indicated in step 30.

From the mechanical analysis and comparisons of steps 26-28 and the computerized data analysis of step 25, the optimal implant characteristics for the patient are determined in step 30, including at least some of the parameters of implant length and diameter, implant shape, implant material and composition, identity and number of vertebrae to fuse, including upper and lower instrumented vertebrae, and position and orientation within the instrumented vertebra. All of the obtained and calculated data are again subjected to analysis by at least some of artificial intelligence, big data, retrospective and actuarial statistical analysis 25 to obtain a numerical output of expected long-term stress on the bone-implant system. Furthermore, an acceptable range of stress scores for long-term survival of the implant is selected for the individual subject. Once an implant is chosen as compatible and acceptable for this patient, it is included in a narrower subset of implants with acceptable scores. From this subset, the best single or few implants with the best shape, i.e., lowest stress scores, are used for the actual instrumentation procedure.

Factors that contribute to the selection of acceptable stress include the subject's age, bone density, and anticipated activity level. For example, an active child might be permitted a lower allowable long-term stress score than a less active elderly person, because the active child would be expected to place more daily post-operative stress on the bone-implant system.

Figure 3:
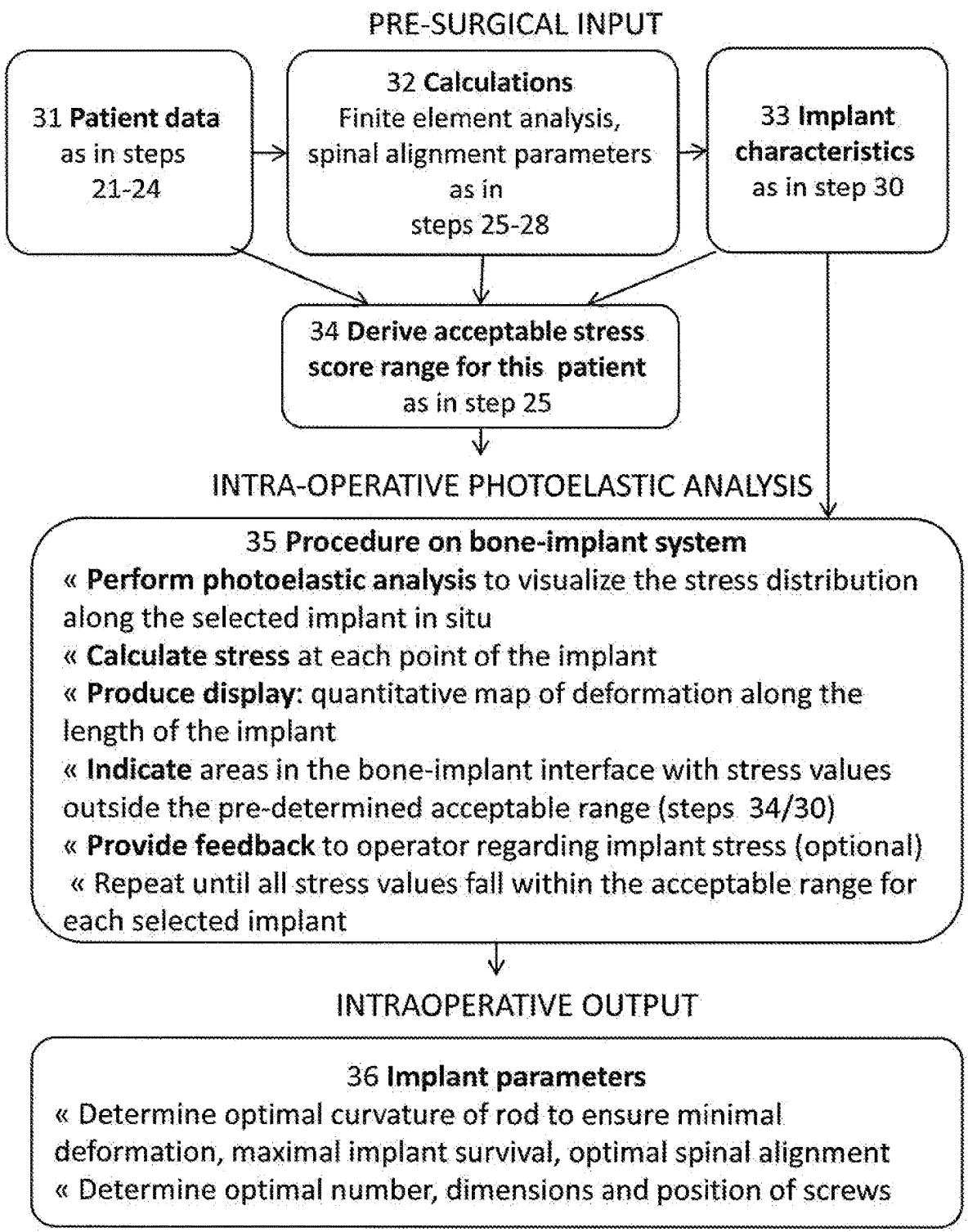
FIG. 3 shows a schematic rendering of the method of integration of the pre-operative virtual results of FIG. 2, with the intra-operative physical stress analysis of the bone-implant system as performed by the system of FIG. 1.

Reference is now made to FIG. 3, which shows a schematic rendering of the method of integration of the pre-operative virtual results of FIG. 2, with the intra-operative physical stress analysis of the bone-implant system as illustrated in the method of FIG. 1, to produce output optimizing bone-implant integration and function for long term survival. Preoperative demographic, clinical and other relevant data are collected 31 as described in steps 21-24. From the acquired 2D or 3D images, generally CT studies but possibly also X-ray, MRI or a combination with dynamic motion studies, spinal alignment parameters are determined and finite element analysis is performed 32 as described in steps 25-29. In step 33, the optimal implant selected in step 30 is then used in the actual surgical procedure. Additionally, from these analyses (31-33) and from the results of step 30, an acceptable stress score range is determined for the individual patient in step 34. During the surgical procedure, in step 35, photoelastic or other stress analysis is performed on the implant as instrumented to the bone. Continuous stress along the length of the implant is displayed on a monitor or other display device, and areas of the bone-implant interface with stress scores higher than the predetermined acceptable range are identified, by one of several methods, such as color change, shading intensity, and auditory output. Feedback is optionally provided to the surgeon, who can decide to remove the implant and modify its shape and contour; change the implant to one with different properties: diameter, length, material; or use fewer pedicle screws, all as shown in step 36. The process is iterative, such that the procedure can be repeated until stress analysis indicates that stress scores along the entire length of the implant fall within the acceptable range. In one exemplary implementation, the implant is covered with a photoelastic coating and stress is measured by photoelastic analysis. Further details of the exemplary photoelastic, real-time and long-term stress scales are shown in FIG. 5 below. The goal of the procedure is to produce an implant with optimal curvature in order to ensure minimal deformation, maximal implant survival and best surgical outcome, in the form of optimal spinal alignment.

Figure 4:
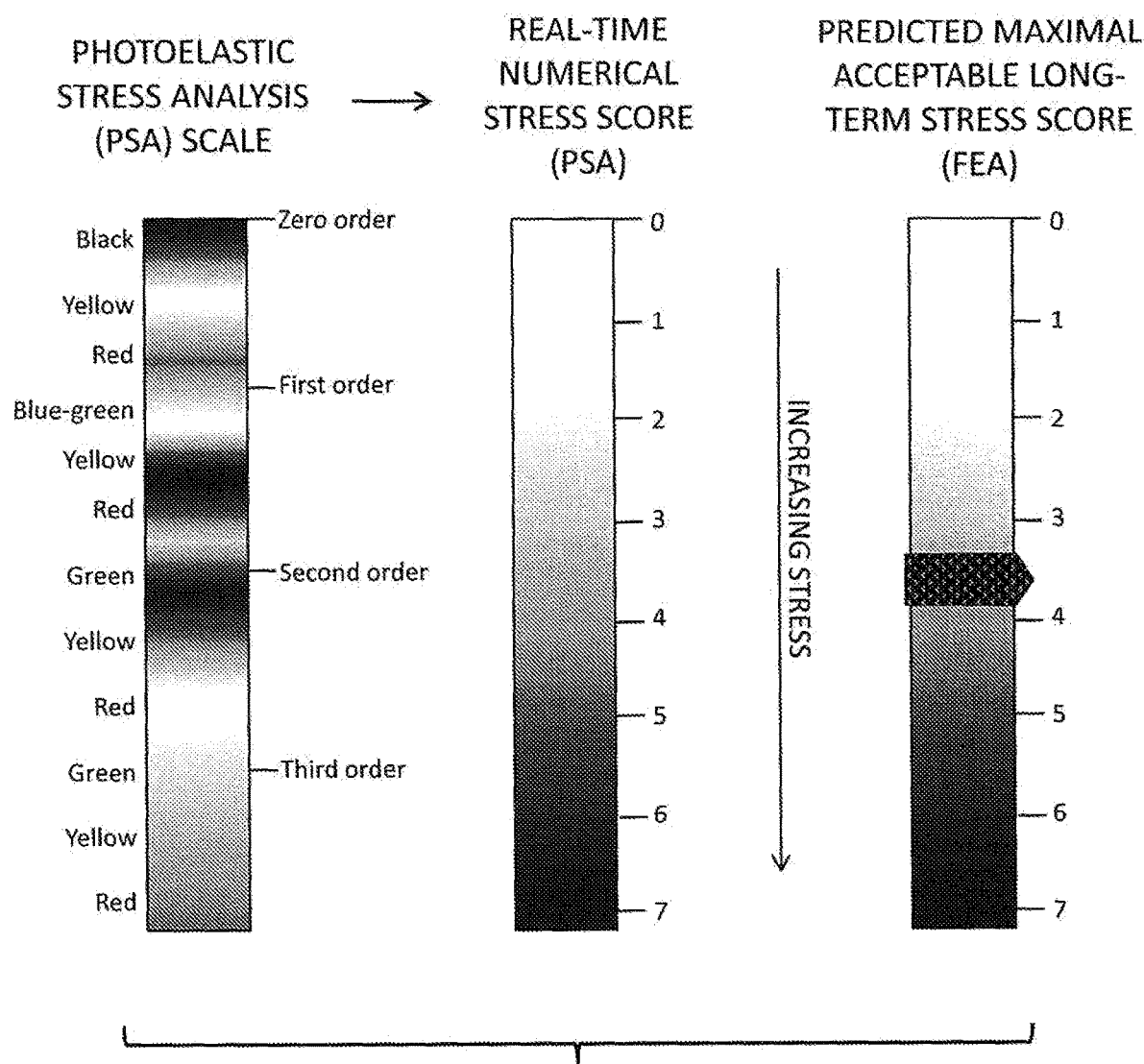
FIG. 4 which depicts a comparison of three corresponding scales for measuring short and long-term stress on a bone-implant configuration.

Reference is now made to FIG. 4, which depicts three corresponding scales for measuring stress on the bone-implant system. On the left side of the drawings, there is shown a representation of the intraoperative stress analysis, in this embodiment a photoelastic stress scale, which appears as a colored spectrum with zero, first, second, and third orders of stress shown. The color-coded photoelastic stress scale may be converted by the camera control system, into a numerical, pseudo-colored, or graded-intensity linear scale indicating increasing stress. This is the scale that may be shown on the display intraoperatively, as in the middle drawing. On the right side of the diagram is the stress scale as determined by the preoperative finite element analysis with the maximum predicted acceptable long-term stress for a given patient indicated by the pointed bar at a determined point on the scale. All scales show increasingly higher stress from the upper to lower aspects of the scale, as indicated by the vertical arrow. The numerical values on each scale indicate equivalent levels of stress among the various scales. In other implementations, different methods of measuring stress may be used and the corresponding scale likewise coordinated to the stress levels shown on the finite element analysis scale.

Figure 5A:
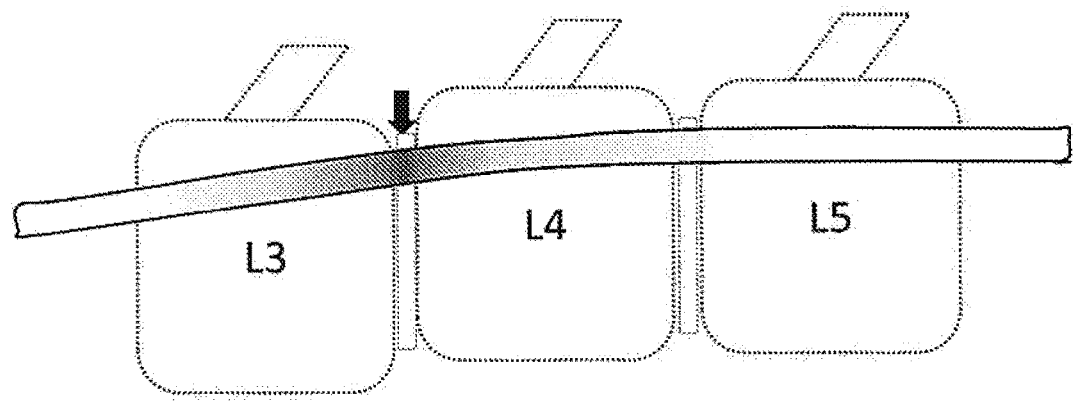
FIGS. 5A to 5C illustrate schematically photoelastic stress analysis of an implant during the stress of instrumentation.
Figure 5B:
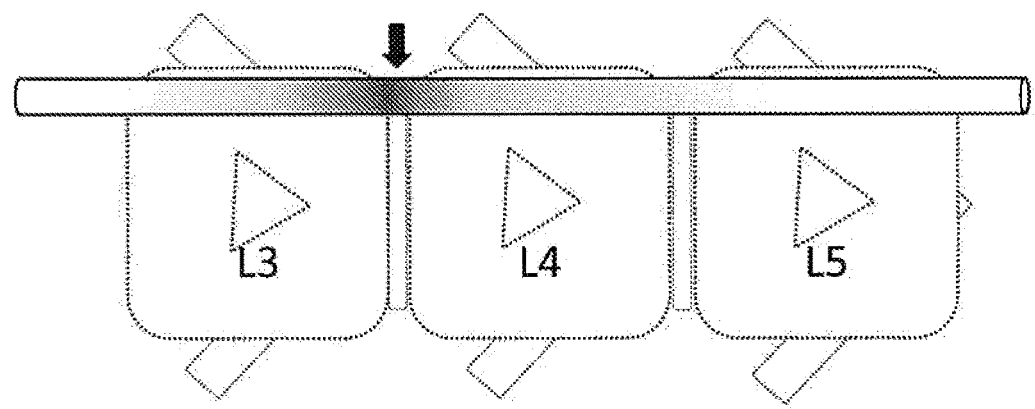
Figure 5C:
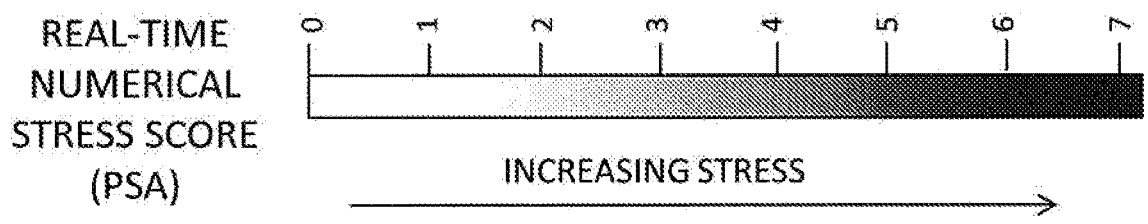

Reference is now made to FIGS. 5A to 5C, which illustrate schematically an implant undergoing photoelastic analysis during the stress of instrumentation. In FIG. 5A, an implant is shown in lateral view as it lies inside the instrumented vertebrae, in this case lumbar vertebrae L3, L4, and L5. FIG. 5B shows the bone-implant system from an anterior-posterior view. In both FIG. 5A and FIG. 5B, the arrow represents the maximum force on the implant at the point of bending, where the pedicle screws attach the implant to vertebra L3-L4. The photoelastic force is shown as shading and quantitated in the corresponding scale in FIG. 5C. Higher stress is represented by darker shading in the photoelastic analysis. The use of photoelastic analysis is understood to be only one implementation of the method, which is not intended to be limited thereto, and the stress could be measured using any method other than photoelastic analysis. In further implementations, the implant may be fitted with a series of sensors for long-term monitoring of stress. Such sensors may be strain gauges, may be of the fiber Bragg grating type, or any other convenient stress sensor. Further embodiments may include sensors on the screw saddles, rods, or any other part of the bone-implant system.

Figure 6A:
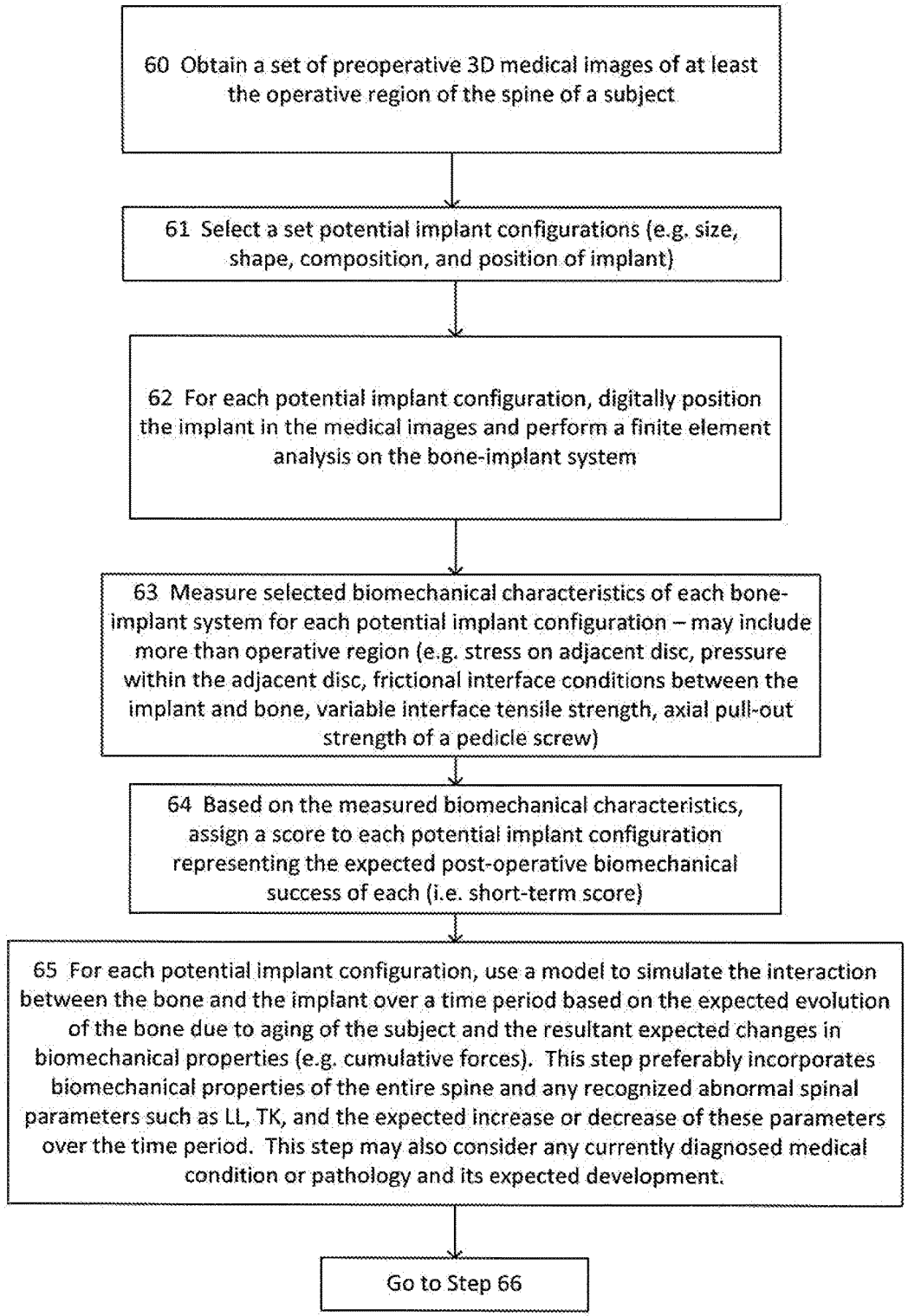
Figure 6B:
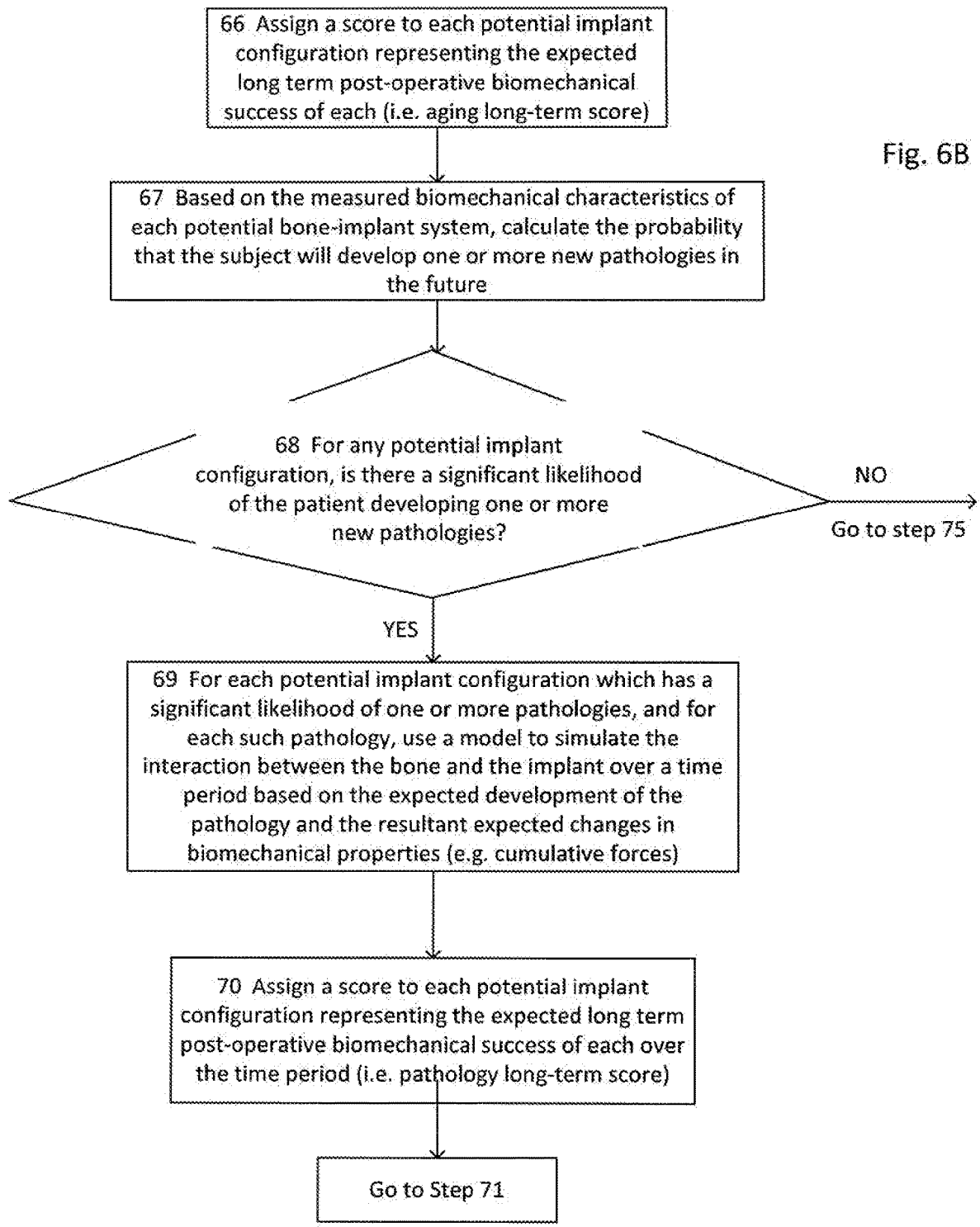

Reference is now made to FIG. 6A-C, which detail each step of the preoperative virtual bone-implant analysis of FIGS. 2 and 3, illustrating how the optimal implant is selected. As an overview of the complete method, a set of 3D medical images of at least the operative region of the spine of a subject is obtained. From these images and from additional patient data detailed above and in FIG. 2, a set of potential implant configurations (size/length, shape/diameter, composition) is selected. For each potential implant configuration, the implant is digitally positioned in the medical images and a finite element analysis on the bone-implant is performed. Selected biomechanical characteristics of each bone-implant system are measured for each potential configuration; this may include more than one operative region of the spine; for example, in some spinal deformities, it is necessary to instrument a section of both or all cervical, thoracic, and lumbar segments of the spinal column. From the potential configurations, the implant(s) of optimal biomechanical characteristics is selected, and the best predicted curvature of the implant determined. A stress score based on the interaction of the implant curvature relative to the patient's anatomy is determined, this being an immediate post-operative theoretical short-term score, since it does not yet use any database information about expected lifetime of the implant under the given conditions. Based on the patient's individual parameters (age, weight, Z-score from bone density scan, disease progression), and combining with the data of implant survival obtained from a large database of subjects with similar spinal distortion problems, the allowable range of stress scores compatible with long-term implant success is selected. In the intra-operative stage now, the implant is bent to the pre-specified curvature, according to anatomical constraints of the patient. The implant is then fixed on the patient's spine, and the stress measured in situ. A convenient method of doing this is by use of using an imaging device with an optical system and controller able to determine levels of photoelastic stress, using a photoelastic coating applied to the implant. Based on the stress measurements, the curvature of the implant is modified and the stress analysis is repeated until a shape is obtained that falls within the predetermined acceptable stress score range. Using the allowable stress score, the optimal curvature of the implant for long-term success of the operation is determined.

A number of variations to the invention for solving specific clinical scenarios are now discussed. If the pre-instrumented spine is highly deformed, ideal anatomical alignment of the bone-implant system may place great stress upon it. Excess stress is prone to cause the instrumentation to fail: the implant(s) will either fail to integrate, or in extreme cases, even break. Pullout of pedicle screws may also occur if the stress on the bone-implant system is greater than the force holding the screw in the vertebral pedicle. Thus, the prediction program compares and evaluates the combination of preoperative implant characteristics and allowable stress to achieve a long-lasting successful bone-implant integration and survival.

In summary, the allowable preoperative stress score as determined by the finite element analysis is used in conjunction with the predictive epidemiological and actuarial data obtained from the statistical analysis and artificial intelligence learning. These data are combined to determine the acceptable stress score range likely to be compatible with long-term survival of the implant for an individual subject. This model is then further refined by measuring the stress in vivo using the above selected implant configurations, and further comparing with allowable stress scores to further improve the prediction assessment of long-term success of the implant.

Referring now to the details of the complete prediction method, as shown in FIGS. 6A to 6C, the steps in this exemplary prediction model may include:

In step 60, obtaining a set of preoperative 3D medical images of at least the operative region of the spine of the subject In step 61, selecting a set of potential implant configurations, including for instance, size, shape, composition, and position of the implant.

In step 62, for each potential implant configuration, digitally positioning the implant in the medical images and performing a finite element analysis on the bone-implant system In step 63, measuring selected biomechanical characteristics of each bone-implant system for each potential implant configuration—may include more than one operative region, such as stress on adjacent discs, pressure within the adjacent discs, frictional interface conditions between the implant and bone, variable interface tensile strength, axial pull-out strength of a pedicle screw.

In step 64, based on the measured biomechanical characteristics, assigning a score to each potential implant configuration representing the expected post-operative biomechanical success of each potential implant, i.e. a short-term score.

In step 65, for each potential implant configuration, using a model to simulate the interaction between the bone and the implant over a time period based on the expected evolution of the bone due to aging of the subject and the resultant expected changes in biomechanical properties, such as from cumulative forces. This step preferably incorporates biomechanical properties of the entire spine and any recognized abnormal spinal parameters such as LL, TK, and the expected increase or decrease of these parameters over the time period. This step may also consider any currently diagnosed medical condition or pathology and its expected development.

Moving now to FIG. 6B, in step 66, a score is assigned to each potential implant configuration representing the expected long term post-operative biomechanical success of each, this being the aging long-term score.

In step 67, based on the measured biomechanical characteristics of each potential bone-implant system, the probability is calculated that the subject will develop one or more new pathologies in the future.

In step 68, a decision is taken for each potential implant configuration, as to whether there is a significant likelihood of the patient developing one or more new pathologies. Should the result be in the negative, the method then moves to the final step 75, in which the optimal implant configuration from the set of selected potential implant configurations is calculated, based on the weighted clinical relevance of at least some of: (i) all calculated short-term scores, (ii) all calculated aging long-term scores, (iii) all calculated pathology long-term scores (if any), (iv) all calculated scenario long-term scores (if any), (v) any calculated probabilities of the subject developing pathologies, and (vi) any calculated probabilities of selected scenarios, such as by using conditional probabilities.

On the other hand, if there is found to be a significant likelihood of the patient developing a new pathology, then in step 69, for each potential implant configuration which has a significant likelihood of one or more pathologies, and for each such pathology, use is made of a model to simulate the interaction between the bone and the implant over a time period based on the expected development of the pathology and the resultant expected changes in biomechanical properties, such as cumulative forces.

In step 70, a score is now assigned to each potential implant configuration representing the expected long term post-operative biomechanical success of each implant configuration over the time period, this being the pathology long-term score.

Moving now to FIG. 6C, in step 71, there is considered whether the subject will be undergoing one or more scenarios in the future that may have an impact on the biomechanical properties of a bone-implant system, such as expected therapeutic intervention including medicine or additional surgery, possible lifestyle changes, requiring a wheelchair or cane, or the like.

Should the result be in the negative, the method then moves to the final step 75, as described above, and concludes the selection process. On the other hand, if some such future change is expected, then in step 72, the probability of the occurrence of each scenario for each potential implant configuration is calculated.

In step 73, for each such potential implant configuration for which there is a significant probability of such a disruptive occurrence, use is made of a model to simulate the interaction between the bone and the implant over a time period based on the expected scenario and the resultant expected changes in biomechanical properties, such as represented by the cumulative forces.

In step 74, a score is then assigned to each potential implant configuration representing the expected long term post-operative biomechanical success, over the time period, this being the long-term score for that expected set of circumstances.

Finally, in step 75, a calculation is performed on that optimal implant configuration from the set of selected potential implant configurations, based on the weighted clinical relevance of at least some of: (i) all calculated short-term scores, (ii) all calculated aging long-term scores, (iii) all calculated pathology long-term scores, if any, (iv) all calculated scenario long-term scores (if any), (v) any calculated probabilities of the subject developing pathologies, and (vi) any calculated probabilities of selected scenarios (i.e. using conditional probabilities).

In some clinical scenarios, it may be desirable to perform the intra-operative modeling of FIG. 3 based on long-term predictions of anticipated progressions in the pathology or clinical status of the patient. This is illustrated by one exemplary method shown in FIG. 7. In such a situation, the implant would be inserted as described in the steps of FIG. 3, optimizing in step 76, the configuration based on actual stress analysis performed intraoperatively, as previously shown in steps 34 and 35 of FIG. 3. Before finalizing the configuration, an additional modeling step is included using the long-term prediction described in FIG. 6A-C. Modeling in this application then takes into account the statistical probability of the patient developing specific bone-related pathologies over time, and anticipated changes in lifestyle or independence in activities of daily living, as illustrated in steps 77. In step 78, these predictive elements can now be used before or during the operation to shape the implant and determine optimal number, position, and size of pedicle screws, interbodies, and other rod-associated instrumentation. Each of these modifications increases the probability of long-term success of the bone-implant system for a given patient. For example, the surgeon may choose to allow higher stress on the bone-implant system to optimize spinal alignment, in exchange for limiting the range of motion or allowed activities postoperatively. Being able to predict the statistical probability of a given scenario optimizes the combination of long-term survival of the bone-implant system and subject functionality.

In step 79, in order to improve long-term performance of the implant, if the desired stress score range has not been achieved, the implant may then be removed or its shape, size, composition and position adjusted, or even an additional implant incorporated into the bone-implant system, until an implant configuration falling within acceptable stress score range is achieved To conclude this implementation of the methods of this disclosure, in step 80, this procedure is repeated until an optimal implant configuration is achieved, ensuring long-term success of the bone-implant system taking into account anticipated progressive pathology, and changes in the mobility of the subject.

While the embodiments described here within primarily concern intervertebral rod implants, similar planning, prediction, and pre- and intraoperative stress analysis may be applied to other elements of the instrumentation including pedicle screws and interbodies, if suitable stress measurement of these components can be applied.

Figure 8:
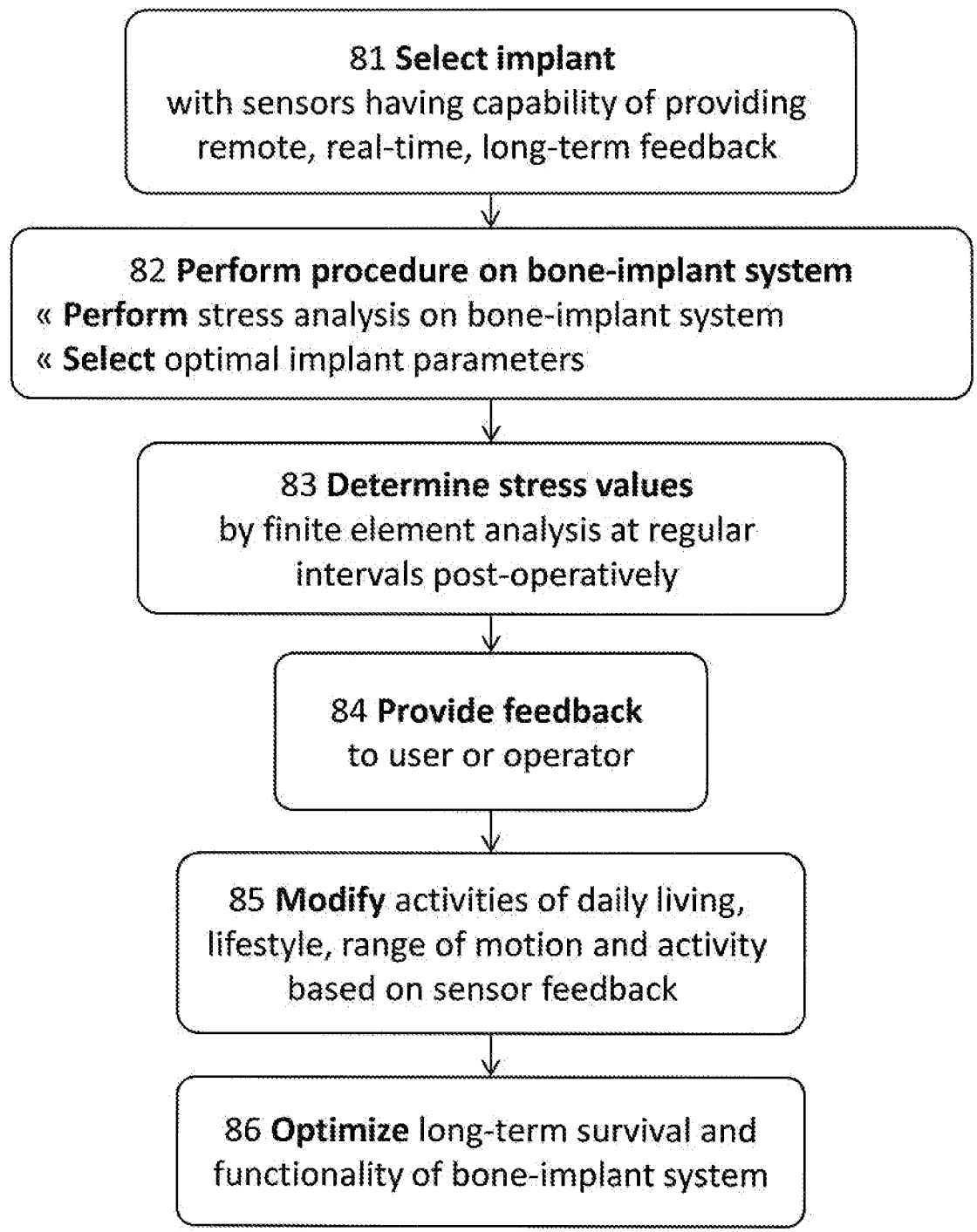
FIG. 8 illustrates a method of long-term follow up of the bone-implant system to determine continued successful function of the system, to predict and prevent undesirable consequences of excessive stress placed on the system.

Finally, in a further clinical scenario, it may be desirable to obtain long-term follow up of the bone-implant system to determine continued successful function of the system, to predict and prevent undesirable consequences of excessive stress placed on the system. Such a method is illustrated in FIG. 8. In such a method, in step 81, the surgeon may implant hardware equipped with sensors for providing to the user or surgeon, remote feedback of the stress situation in real time. Such feedback 84 would be provided post-operatively by performing finite element analysis on the bone-implant system at regular intervals of time as shown in step 83. The surgeon or user can determine the likelihood of occurrence of various undesirable scenarios if the stress level exceeds the recommended value over short and long time periods. This information can be used to counsel the subject regarding possible post-operative lifestyle choices 85, with the final goal to be long-term survival and optimal functionality of the bone-implant system 86.

Figure 9:
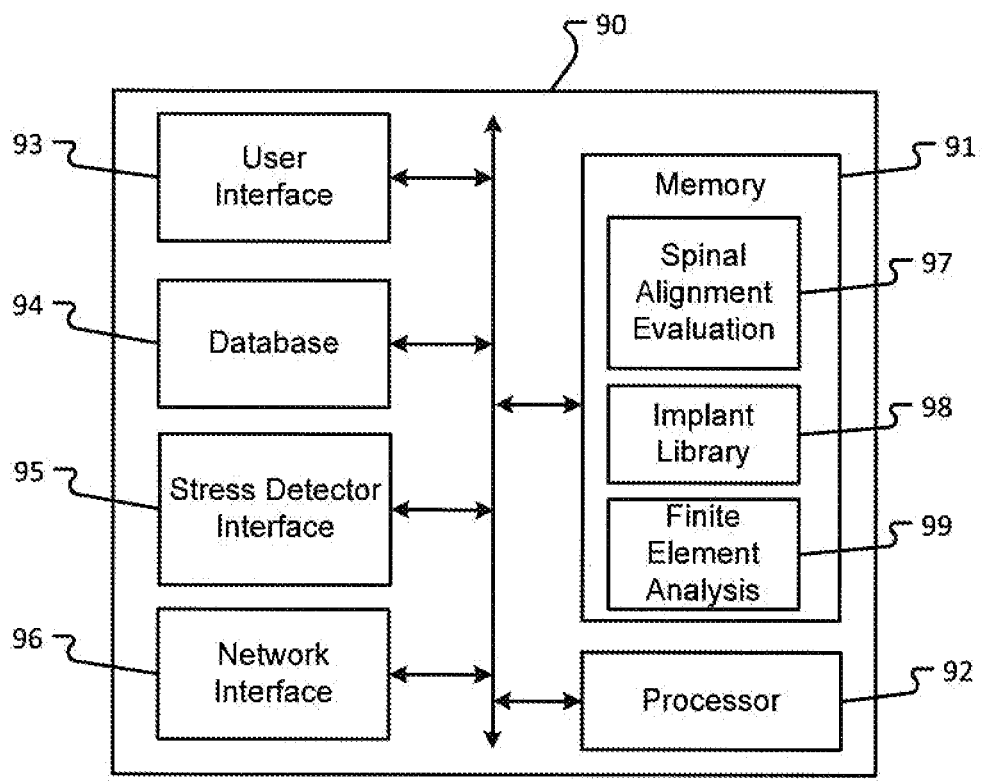
FIG. 9 illustrates the structure of a controller for use in a system capable of implementing methods of the present disclosure.

Systems according to embodiments of the present disclosure may comprise a controller 90, as shown in FIG. 9. The controller 90 comprises a processor 92, a memory 91, a user interface 93, one or more databases 94, one or more stress detector interfaces 95, and a network interface 96.

Reference is now made to FIG. 9, which illustrates the structure of a controller for use in a system capable of implementing methods of the present disclosure.

The memory 91 may be any computer-readable, non-transitory storage medium. The memory 91 may store information and/or instructions 97 needed for spinal alignment evaluation (e.g., to determine spinal alignment parameters from one or more pre-operative images or intra-operative images), a digital library 98 of parameters associated with a plurality of available implants; and instructions and/or information 99 necessary for conducting finite element analysis on a digital model of an implant-bone combination.

The processor 92 may be an application specific integrated circuit (ASIC), microprocessor, programmable controller, or the like. The processor 92 executes the instructions stored in the memory 91.

The controller 90 may receive operating instructions, pre-operative images, and/or other data via the user interface 93. The user interface 93 may be or comprise software and/or hardware for receiving information, including, for example, a keyboard, a mouse, a touchscreen, a wireless transceiver, and/or a wired transceiver.

The database 94 may comprise patient demographic data and/or preoperative clinical data.

The stress detector interface 95 may comprise hardware and/or software useful for receiving stress measurements from a stress detector, and for providing such measurements to the processor 92.

The network interface 96 may be or comprise a wired or wireless communication transceiver and/or other hardware and/or software that enables the controller 90 to communicate with one or more other devices via a network. The network may be a local area network, a wide area network, or any other network. The network may be, for example, the Internet.

It is appreciated by persons skilled in the art that the present invention is not limited by what has been particularly shown and described hereinabove. Rather the scope of the present invention includes both combinations and sub-combinations of various features described hereinabove as well as variations and modifications thereto which would occur to a person of skill in the art upon reading the above description and which are not in the prior art.

We claim:

1. A method of determining an optimal, long-term orthopedic implant configuration for a spinal alignment correction procedure in a subject, comprising:
   (a) based on a set of preoperative medical images, determining initial values and a desired corrected set of values of selected spinal alignment parameters;
   (b) selecting at least one potential implant for correcting the selected spinal alignment parameters;
   (c) digitally positioning, in the set of preoperative medical images, the at least one potential implant for correcting the selected spinal alignment parameters, to create at least one virtual configuration of at least one potential bone-implant combination;
   (d) determining an acceptable long-term stress score range for the at least one virtual configuration based on (i) clinically relevant data of the subject, and (ii) similarly characterized cases from a medical database;
   (e) for the at least one virtual configuration, (i) performing finite element analysis on the at least one potential implant to determine stress scores along an extent of the at least one potential implant; and (ii) calculating expected corrected values of the selected spinal alignment parameters;
   (f) select an implant from the at least one potential implant, which minimizes the long-term stress score;
   (g) intraoperatively, inserting the selected implant into a spine of the subject, the inserted implant being adapted to have at least one mode of stress detection;
   (h) using the at least one mode of stress detection, intraoperatively measuring a stress score at each point along a length of the inserted implant; and
   (i) modifying the inserted implant and repeating steps (g) to (h) until an implant configuration falling within the acceptable long-term stress score range is achieved.

2. A method according to claim 1, wherein if no implant configuration falling within the acceptable long-term stress score range is achieved, repeating steps (f) to (i) with a second implant from the at least one potential implant, until an implant configuration falling within the acceptable long-term stress score range is achieved.

3. A method according to claim 1, wherein the implant configuration falling within the acceptable long-term stress score range has a combination of corrected spinal alignment parameters, minimum stress score, and maximum long-term survival, to thus provide an optimal long-term orthopedic implant configuration.

4. A method according to claim 1, wherein modifying the inserted implant comprises modifying at least one of a shape, curvature, or orientation of the inserted implant.

5. A method according to claim 1, wherein the inserted implant comprises a photoelastic coating, and the intraoperatively measuring a stress score uses photoelastic analysis of the photoelastic coating to obtain a field pattern of stress of the implant in situ.

6. A method according to claim 1, wherein sensors of a fiber Bragg grating type are used to intraoperatively measure the stress score.

7. A method according to claim 1, wherein tactile force feedback from a surgical robot is used to intraoperatively measure the stress score.

8. A method according to claim 1, wherein stress analysis for the selected implant is carried out using sensors connected to a screw saddle or to a fusion rod.

9. A method according to claim 1, wherein the implant comprises any of pedicle screws, interbodies and rods.

10. A method according to claim 1, wherein at least one of a shape, size, composition, orientation and position of the implant are replaceable by a different implant.

11. A method according to claim 1, wherein potential implant configurations comprise at least one of the shape, size, length, diameter, composition, position and orientation of each implant.

12. A method according to claim 1, wherein the preoperative medical images are at least one two-dimensional or three-dimensional CT, MRI, X-ray, and dynamic motion capture images.

13. A method according to claim 1, wherein spinal alignment parameters comprise at least some of Sagittal/Coronal Cobb, TK, LL, SVA, SS, PI, PT, AVT-T, AVT-L, CD, RAD, Pelvic obliquity.

14. A method according to claim 1, wherein the long-term acceptable stress score is calculated per patient.

15. A method according to claim 1, wherein the implant comprises at least one intervertebral rod and at least two pedicle screws.

16. The method according to claim 1, wherein the implant is selected from the at least one potential implant based on one or more of a shape, a diameter, a length, and a material composition.

17. The method according to claim 1, wherein the implant is selected to correct the selected spinal alignment parameters better than others of the at least one potential implant.

18. The method according to claim 1, wherein the clinically relevant data comprises at least one of (i) past medical history, (ii) age, (iii) BMI, (iv) gender, (v) comorbidity, (vi) ethnicity, and (vii) current clinical status.

19. The method according to claim 1, wherein selection of at least one the implant is based on at least one of: the desired corrected values of the selected spinal alignment parameters, clinical data of the subject, a medical database, and a preoperative plan to correct the spinal alignment parameters.

20. A method according to claim 19, further using at least one of big data analysis, statistical analysis, and modeling of feedback of stress scores for an individual subject according to the long-term stress score.

21. A method according to claim 20, wherein the modeling is based on a database of information collected from subjects undergoing operations for bone-implant systems.

22. A method according to claim 15, using preoperative planning using the finite element analysis to analyze survival of bone-implant system of subjects who return for revision operation of the bone-implant system.

23. A surgical system for determining an optimal long-term orthopedic implant configuration for a spinal alignment correction in a subject, the system comprising:
   a control unit, wherein the control unit comprises:
      (i) a module for finite element analysis of orthopedic configurations;
      (ii) an analytic engine for evaluating a long-term effect of implant configurations using previous cases documented in a large database;
      (iii) a calculating unit for determining spinal alignment parameters from a virtual configuration of a spine corrected using a spinal implant arrangement;
      (iv) a comparator unit for determining whether a predicted stress score of an implant configuration falls within a predetermined acceptable stress score for long term sustainability, the control unit being configured to determine an optimal implant configuration, by:
  (a) based on a set of preoperative medical images, determining initial values and a desired corrected set of values of selected spinal alignment parameters;
  (b) selecting at least one potential implant for correcting the selected spinal alignment parameters;
  (c) digitally positioning, in the set of preoperative medical images, the at least one potential implant for correcting the selected spinal alignment parameters, to create at least one virtual configuration of at least one potential bone-implant combination;
  (d) determining an acceptable long-term stress score range for the at least one virtual configuration based on (i) clinically relevant data of the subject, and (ii) similarly characterized cases from a medical database;
  (e) for the at least one virtual configuration, (i) performing finite element analysis on the at least one potential implant to determine stress scores along an extent of the at least one potential implant; and (ii) calculating expected corrected values of the selected spinal alignment parameters; and
  (f) selecting an implant from the at least one potential implant, which minimizes the long-term stress score; and
a measurement system configured to measure the stress in an implant inserted onto the spine of a subject, the measurement system comprising a camera adapted to determine a stress pattern arising in the implant by analyzing an image of a photoelastic coating on the inserted implant,
the measurement system being thus configured to enable adjustment intraoperatively of the at least one potential implant to minimize its stress score, thereby providing an improved long term orthopedic implant configuration.

24. A method of modeling and predicting long-term success of a spinal implant configuration in a subject, comprising:
  (a) for a plurality of potential implants, calculating a long-term stress score for at least one potential implant based on (i) stress within the at least one potential implant as determined using finite element analysis of a virtual configuration of the at least one potential implant virtually inserted into a preoperative image of a spine of a subject, (ii) calculated values of selected spinal parameters, and (iii) clinical data of the subject and from a database of similar cases;
  (b) determining an acceptable long-term stress score range for the virtual configuration of the at least one potential implant based on (i) clinically relevant data of the subject, and (ii) similarly characterized cases from a medical database;
  (c) when the long-term stress score for the for at least one potential implant does not fall within the acceptable long-term stress score range, selecting another potential implant from the plurality of potential implants, until the stress score of an optimal one of the potential implants falls within the acceptable long-term stress score range;
  (d) intraoperatively inserting the optimal implant into the subject, the implant being adapted to have at least one mode of stress detection;
  (e) using the at least one mode of stress detection to measure a stress at points along the inserted optimal implant to obtain a field pattern of stress of the inserted implant;
  (f) inputting the field pattern of stress to a model to simulate an interaction between the spine and the inserted optimal implant over a given time period to determine expected changes in the field pattern of stress over the given time period;
  (g) based on the expected changes in the field pattern of stress, calculating an optimal shape of the inserted optimal implant that causes the inserted optimal implant to have a minimum long term stress score over the given time period; and
  (h) based on the calculations of step (g), adjusting the inserted optimal implant to the calculated optimal shape.

25. A method for long-term follow-up of bone-implant success in a subject, comprising:
  (a) selecting an optimal implant from a plurality of potential implants based on (i) stress within the plurality of potential implants detected using finite element analysis of a virtual configuration of each of the plurality of potential implants virtually inserted into a preoperative image of a spine of a subject, (ii) calculated values of selected spinal parameters, and (iii) clinical data of the subject and from a database of similar cases;
  (b) determining an acceptable long-term stress score of the optimal implant for the subject;
  (c) intraoperatively inserting the optimal implant into the subject to yield a bone-implant system, the optimal implant being equipped with at least one mode of stress detection able to provide remote, real time measurement of stress on the bone-implant system;
  (d) determining, at regular intervals of time post-operatively, selected spinal parameters by analysis of medical images and by finite element analysis of a field pattern of stress detected with the at least one mode of stress detection;
  (e) providing real-time feedback of the selected spinal parameters and of the field pattern of stress to at least one of the subject and a surgeon; and
  (f) measuring evolution of at least one of the spinal parameters and of the field pattern of stress of bone-implant system.

26. A method according to claim 25, wherein the selected spinal parameters comprise at least one of sagittal/coronal Cobb, TK, LL, SVA, SS, PI, PT, AVT-T, AYT-L, CD, RAD, and pelvic obliquity.

27. A method according to claim 25, further using at least one of big data analysis, statistical analysis, and modeling of the feedback of stress scores for an individual subject according to the long-term stress score.

28. A method according to claim 27, wherein the modeling is based on a database of information collected from subjects having undergone spinal implant operations.

29. A method according to claim 25, using preoperative planning using the finite element analysis to analyze survival of the bone-implant system of subjects who return for revision operation of the bone-implant system.

* * * * *